United States Patent [19]
Myers et al.

[11] Patent Number: 5,358,516
[45] Date of Patent: Oct. 25, 1994

[54] IMPLANTABLE ELECTROPHYSIOLOGY LEAD AND METHOD OF MAKING

[75] Inventors: David J. Myers, Camp Verde; John M. Williams, Flagstaff, both of Ariz.

[73] Assignee: W. L. Gore & Associates, Inc., Newark, Del.

[21] Appl. No.: 988,998

[22] Filed: Dec. 11, 1992

[51] Int. Cl.⁵ .............................. A61N 5/04
[52] U.S. Cl. ................................... 607/116
[58] Field of Search .................. 128/784–786; 607/116, 121, 122

[56] References Cited

U.S. PATENT DOCUMENTS

| | | | |
|---|---|---|---|
| 3,035,583 | 5/1962 | Hirsch et al. | 128/784 |
| 3,568,660 | 3/1971 | Crites et al. | 128/786 |
| 4,033,355 | 7/1977 | Amundson | 128/784 |
| 4,352,360 | 10/1982 | King | 128/786 |
| 4,573,480 | 3/1986 | Hirschberg | 128/784 |
| 4,840,186 | 6/1989 | Lekholm et al. | 128/784 |
| 4,947,866 | 8/1990 | Lessar et al. | 128/784 |
| 4,972,846 | 11/1990 | Owens et al. | 128/784 |
| 5,103,837 | 4/1992 | Weidlich et al. | 128/784 |

FOREIGN PATENT DOCUMENTS 2328996 12/1973 Fed. Rep. of Germany.

Primary Examiner—William E. Kamm
Attorney, Agent, or Firm—Wayne D. House

[57] ABSTRACT

An implantable lead in the form of an electrical conductor wire having an insulating layer of impervious plastic surrounding the surface of the electrical conductor wire and further having an exterior surface covering of porous PTFE. The impervious plastic insulating layer is preferably a thermoplastic and most preferably a thermoplastic fluoropolymer such as ETFE, FEP or PFA. The exterior surface covering of porous PTFE offers improved flexibility and biocompatibility in comparison to conventional lead wires having silicone exterior surfaces, while the impervious plastic insulating layer prevents loss of insulating integrity resulting from wetting out of the porous PTFE exterior surface by body fluids. Methods of making the implantable lead are also described.

22 Claims, 6 Drawing Sheets

# IMPLANTABLE ELECTROPHYSIOLOGY LEAD AND METHOD OF MAKING

FIELD OF THE INVENTION

This invention relates to the field of implantable electrical leads for use with various implantable electrical devices such as cardiac pacemakers, defibrillators and other electrotherapy applications, and to their method of making.

BACKGROUND OF THE INVENTION

Conventional implantable leads for use with implantable electrical devices such as cardiac pacemakers and defibrillators are typically constructed of at least one electrical conductor that is preferably wound into a helical form and having an outer insulation layer of tubular form coaxially surrounding the electrical conductor. The tubular insulation is most commonly of an elastomeric material such as silicone or polyurethane. The combination of a helically wound conductor with elastomeric outer insulation provides these conventional constructions with a substantial amount of potential elastic deformation in the direction of the length of the lead.

The fundamental requirements of implantable leads are that they must have excellent mechanical integrity, insulating properties and biocompatibility, and must be flexible with a long flex life to accommodate attachment to a beating heart or other anatomical flexures.

Conventional implantable leads have several disadvantages. The silicone or polyurethane outer coverings are not ideally biocompatible and are frequently known to provoke adverse tissue reactions over time. They are also known to fail due to exposure to blood chemistry. Silicone leads result in cases of acute allergic responses in some patients. Silicone leads promote formation of a fibrous sheath which can ultimately encapsulate the lead. Polyurethane leads frequently fail due to environmental stress cracking and metal ion oxidation. Additionally, these leads are known to break during attempts to remove them from implanted patients by the application of a tensile force. In these cases the remaining portion must be abandoned within the patient's body or must be surgically removed.

Implantable lead wires using insulation materials other than the conventional silicones or polyurethanes have been described previously. U.S. Pat. No. 4,573,480 describes an implantable electrode lead in the form of a helically wound conductor having a tubular insulating layer surrounding the helically wound wire wherein the tubular insulating layer is porous polytetrafluoroethylene (hereinafter PTFE) having a pore size limited to a maximum size described as "being essentially impervious to body fluids to prevent tissue growth thereon." This pore size is described as being not larger than 4 microns. While pore sizes of this range and smaller are known to preclude cellular ingrowth, the material remains pervious to body fluids which will wet out such an insulating layer shortly after implantation. The result is that the effectiveness of the electrical insulation is destroyed. This patent also teaches that the tubular porous PTFE insulating layer may alternatively be provided with an outer covering of smooth and impervious material. While this alternative construction prevents the wetting out of the porous PTFE layer by body fluids, it loses the biocompatible advantage provided by the blood or tissue contacting outer surface of porous PTFE.

SUMMARY OF THE INVENTION

The present invention is an implantable electrophysiology lead comprising at least one electrical conductor wire having an electrically insulating layer of impervious plastic surrounding the electrical conductor wire, and an exterior surface covering of porous PTFE tubing. Methods of making the invention are also described.

The at least one electrical conductor wire is preferably a helically wound conductor for applications requiring good flexibility with good flex life. The at least one helically wound conductor wire used with the present invention may be a single conductor or alternatively may be multiple-filar if more than one conductor is required for a desired application. Multiple conductors of either straight or helical orientation will require that the individual conductors be separately insulated from each other, preferably by a layer of insulation covering the surface of each individual conductor. In the case of helically wound conductors, the insulation covering the surface of the individual conductors is preferably applied to each conductor surface prior to helical winding of the conductors. The insulation covering the surface of the individual conductors is preferably a thermoplastic fluoropolymer such as ethylenetetrafluoroethylene copolymer (hereinafter ETFE), fluorinated ethylene propylene (hereinafter FEP), or perfluoroalkoxy resin (hereinafter PFA) applied as a hot-melt extrusion in a layer as thin as about 0.04 mm.

The porous PTFE exterior surface covering of the leadwire of the present invention provides excellent biocompatibility and excellent flexibility. The layer of impervious plastic insulation between the porous PTFE exterior surface covering and the at least one electrical conductor wire is required to prevent body fluids from penetrating the porous PTFE layer and contacting the electrical conductor wire. By impervious is meant a non-porous material that is not penetrated by body fluids with the result that the effectiveness of the electrical insulation is compromised. Preferred impervious plastic insulations are thermoplastic fluoropolymers such as ETFE, FEP and PFA.

DETAILED DESCRIPTION OF THE INVENTION

Figure 1:
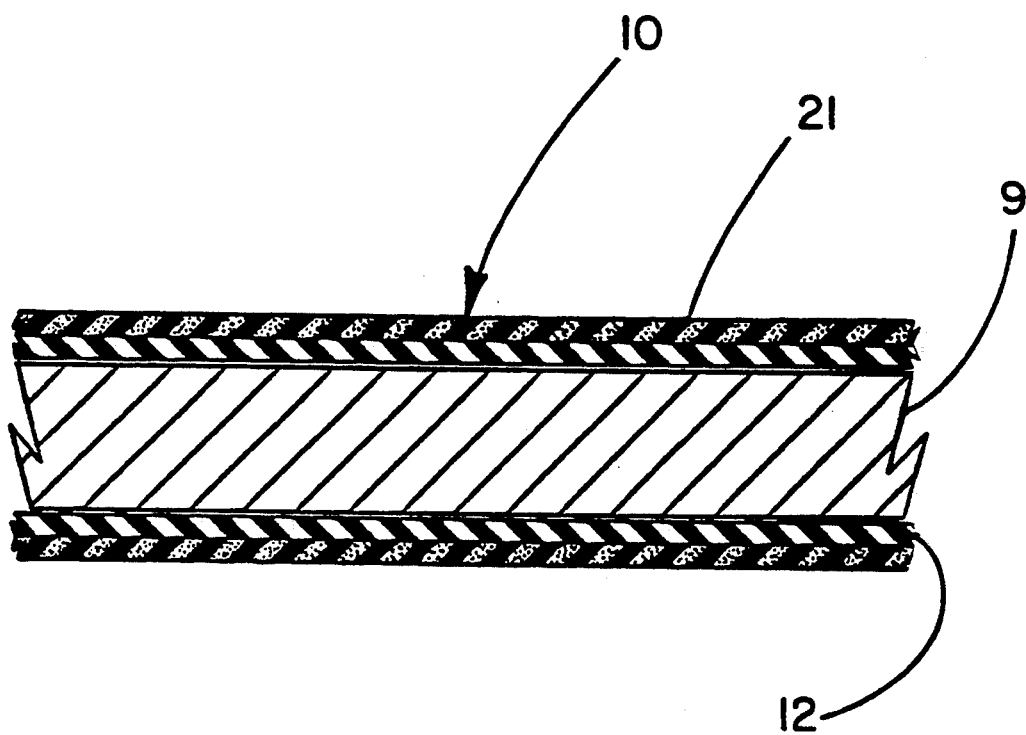
FIG. 1 shows a cross section of an implantable lead of the present invention having an electrical conductor with an insulative covering of an impervious plastic tubing and an exterior covering of porous PTFE tubing for improved flexibility and biocompatibility.

The exterior surface covering of porous PTFE may be in the form of porous PTFE tubing in a coaxial relationship with the at least one electrical conductor wire. The term coaxial is herein used in relationship to the longitudinal axis of the helix formed by the at least one helically wound conductor or alternatively in relationship to the longitudinal axis or axes of the at least one conductor wire oriented in straight fashion rather than helically wound. The use of porous PTFE tubing in this embodiment requires the use of an additional intermediate coaxially oriented tubular layer of an impervious plastic insulation between the at least one conductor wire and the porous PTFE tubing. Preferred materials for this layer include silicone and thermoplastic fluoropolymers such as ETFE, FEP and PFA.

The exterior surface covering of porous PTFE is preferably in the form of a helically wrapped tape wherein the tape is in the form of a laminate of porous PTFE and a non-porous thermoplastic which is preferably a non-porous thermoplastic fluoropolymer such as FEP. The laminated tape is helically applied with overlapping edges and with the porous PTFE oriented outwardly so that it comprises the exterior surface of the implantable lead wire. The laminated tape may be applied in this fashion about the exterior surface of an electrical conductor wire wherein the inward facing non-porous FEP layer of the laminate comprises the impervious plastic, electrically insulating layer. This construction is heated during manufacture to above the melt point of the impervious plastic electrically insulating layer and preferably to less than the sintering temperature of the porous PTFE, that is, to less than about 342 degrees C. This heating step causes the impervious plastic electrically insulating layer to thermally bond to adjacent components of the construction and thereby guarantee the integrity of the impervious plastic electrically insulating layer.

In an alternative embodiment the laminated helically wound tape is coaxially applied so that the outer surface of the at least one conductor is in contact with the PTFE side of the laminated tape. The non-porous FEP side of the laminated tape faces outwardly and is thermally bonded to the inner surface of a porous PTFE tubing which in turn comprises the exterior surface of this embodiment.

The fibril length of the porous PTFE must be adequate to provide the necessary amount of flexibility for the intended application and preferably should be of adequate size to present an acceptable biocompatible surface to the blood chemistry to which the outer surface will be exposed. The preferred fibril lengths are greater than about 4 microns and most preferably greater than about 10 microns. Porous PTFE of fibril lengths greater than about 10 microns has been proven to be acceptable for use in situations involving exposure to blood chemistry through a long history of use in vascular graft applications. Fibril length is measured as taught by U.S. Pat. No. 4,972,846.

The porous PTFE used for either tubular coverings or as the porous PTFE layer of the laminated fluoropolymer tape is preferably porous expanded PTFE made according to the teachings of U.S. Pat. Nos. 4,187,390 and 3,953,566. The tubular covering of porous expanded PTFE may be provided with stretch characteristics in a similar manner to that taught by U.S. Pat. Nos. 4,877,661 and 5,026,513.

FIG. 1 describes a cross section of an implantable lead 10 according to the present invention wherein an electrical conductor 9 is covered by a layer of impervious plastic insulation 12 which prevents fluids including body fluids from reaching the electrical conductor 9. The layer of impervious plastic insulation 12 is preferably a thermoplastic and most preferably a thermoplastic fluoropolymer such as ETFE, FEP or PFA. Alternatively the layer of impervious plastic insulation may be an elastomeric material such as silicone or polyurethane. The exterior surface is provided by a covering of porous PTFE 21 which provides the implantable lead with good flexibility and biocompatibility. While this porous PTFE layer 21 is vulnerable to becoming wet out by body fluids, the integrity of the electrical insulation is maintained by the presence of the impervious plastic insulating layer 12.

Figure 2:
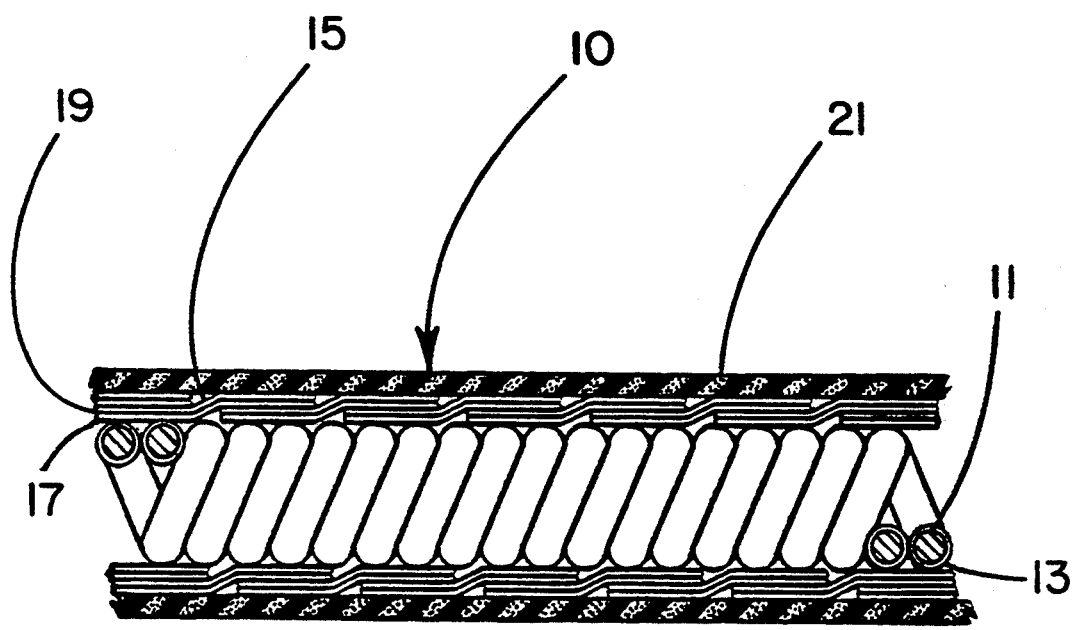
FIG. 2 shows a cross section of an alternative embodiment wherein a thermoplastic insulated helically wound conductor is provided with an insulative covering of a laminated fluoropolymer tape wrapped coaxially around the exterior of the helically wound conductor and further has an additional exterior covering of porous PTFE tubing.

FIG. 2 describes a cross section of an implantable lead 10 according to the present invention. A helically wound conductor 11 is optionally and preferably provided with a thermoplastic insulating layer 13. This layer 13 is preferably a thermoplastic fluoropolymer such as ETFE, FEP or PFA applied by melt extrusion about the outer surface of the conductor 11 prior to winding the conductor into a helical form. The helically wound conductor 11 is subsequently provided with a helically wrapped tape covering 15 oriented coaxially with respect to the helix. Finally, an exterior tubular covering 21 of porous PTFE is applied over the helically wrapped tape covering. The tape covering 15 is a two layer fluoropolymer laminated tape wherein the inner layer 17 of the laminated tape 15 is porous PTFE and the outer layer 19 is a non-porous thermoplastic fluoropolymer adhesive which is preferably FEP. The laminated tape covering 15 is applied about the outer surface of the helically wound conductor by helically winding the tape in an overlapping fashion and subsequently heating the assembly adequately to melt the thermoplastic fluoropolymer and thereby causing the tape covering 15 to adhere to the exterior tubular porous PTFE covering 21.

This construction provides the lead with substantial tensile strength and with good flexibility due to the porosity of the exterior tubular porous PTFE covering 21. Additionally, the porous PTFE offers superior biocompatibility in comparison to conventional elastomeric insulations. The porous PTFE inner surface 17 of the laminated tape 15 also provides a lubricious surface for insertion of the conductor wire after completion of the insulation. The inventive construction also provides excellent insulation properties resulting from the use of the preferred thermoplastic fluoropolymer insulating layer 13 surrounding the conductor. These thermoplastic fluoropolymer insulating layers including ETFE, FEP and PFA may be melt extruded around the exterior of the conductor in a layer as thin as about 0.04 mm.

For cardiac pacer applications, the conductor is preferably a drawn-filled tube material having a silver core representing approximately 43% of the total cross sectional area of the wire with the remaining outer area being MP35N nickel alloy stainless steel. Examples of the lead of the present invention were made using a solid core MP35N conductor wire that had been provided with an insulating layer of ETFE of about 0.04 mm thickness, had a insulated diameter of about 0.2 mm and had been wound into a helix having an outside diameter of about 0.84 mm with a helical pitch in the relaxed state of about 0.43 mm. This wire was obtained from Fort Wayne Metals Research Products Corp., Ft. Wayne, Ind.

The laminated fluoropolymer tape used as the helically wrapped covering is made by a process which comprises the steps of:
 a) contacting a porous PTFE substrate, usually in the form of a membrane or film, with a layer, usually a film of a thermoplastic fluoropolymer;
 b) heating the composition obtained in step a) to a temperature above the melting point of the thermoplastic fluoropolymer;
 c) stretching the heated composition of step b) while maintaining the temperature above the melting point of the thermoplastic fluoropolymer; and
 d) cooling the product of step c).

Figure 3:
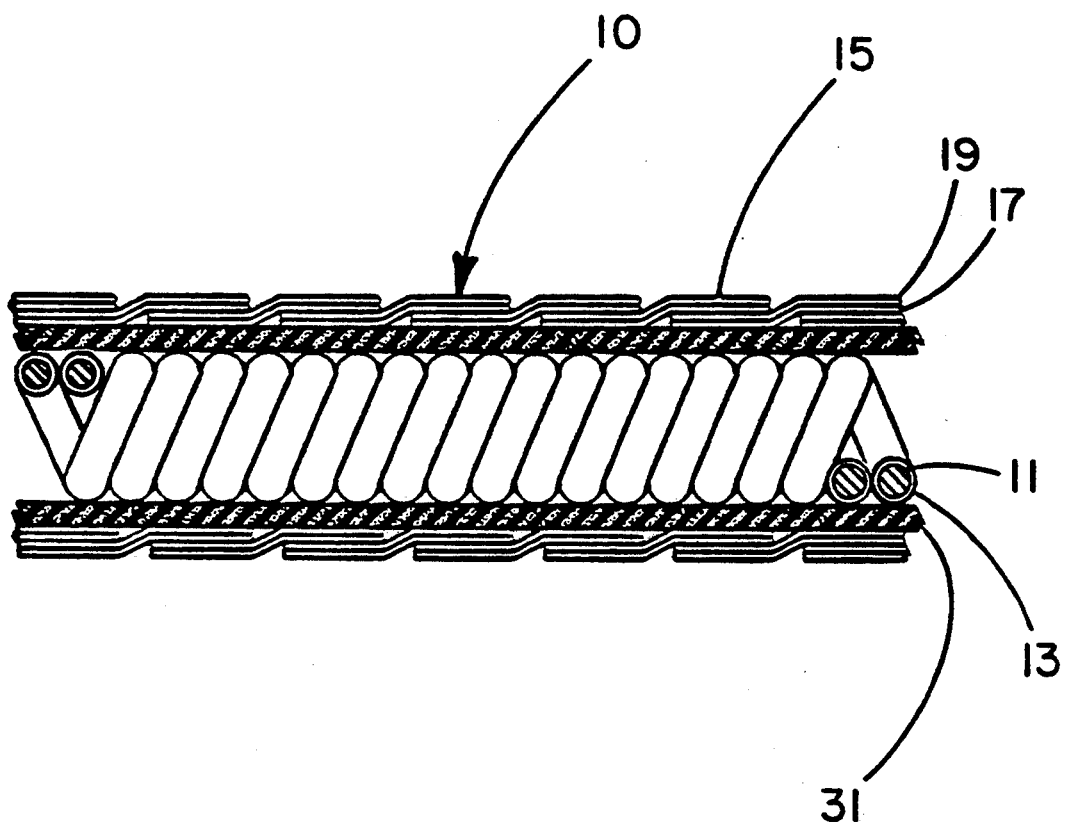
FIG. 3 shows a cross section of an alternative embodiment wherein the thermoplastic fluoropolymer insulated helically wound conductor is provided with a coaxial insulating covering of silicone tubing and an exterior helical wrapping of laminated fluoropolymer tape.

FIG. 3 shows a cross section of an alternative embodiment wherein the helically wound conductor 11 having an optional and preferable layer of thermoplastic insulation 13 is provided with a coaxial insulating covering of silicone tubing 31 and an exterior helical wrapping of laminated fluoropolymer tape 15. In this embodiment, the two layer laminated tape is oriented so that the porous PTFE layer 19 comprises the exterior surface of the lead wire and the non-porous thermoplastic layer 17 of the laminated tape 15 faces the outer surface of the coaxial insulating covering of silicone tubing 31.

Figure 4:
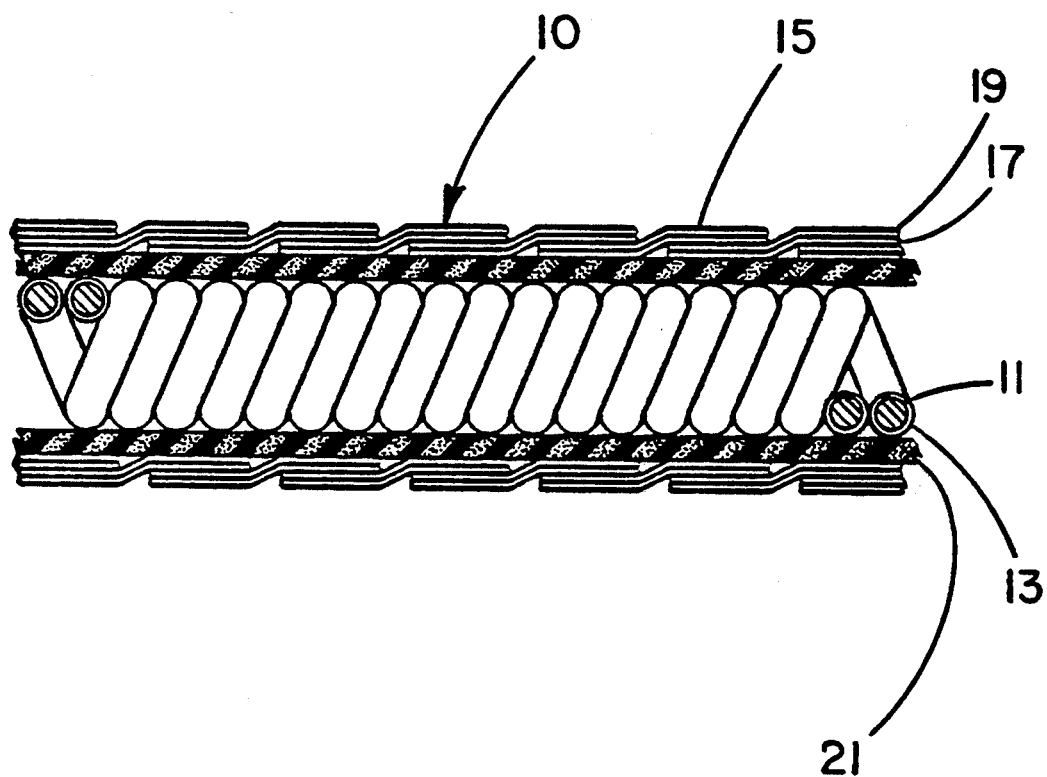
FIG. 4 shows a cross section of an alternative embodiment wherein the thermoplastic fluoropolymer insulated helically wound conductor is provided with a coaxial covering of porous PTFE tubing and an exterior helical wrapping of laminated fluoropolymer tape.

FIG. 4 shows a cross section of an alternative embodiment wherein the helically wound conductor 11 having an optional and preferred thermoplastic insulating layer 13 is provided with a coaxial covering of porous PTFE tubing 21 and an exterior helical wrapping of laminated fluoropolymer tape 15. In this embodiment, the two layer laminated tape 15 is oriented so that the porous PTFE layer 19 comprises the exterior surface of the lead wire and the inner non-porous thermoplastic layer 17 faces the outer surface of the coaxial covering of porous PTFE tubing 21.

Figure 5:
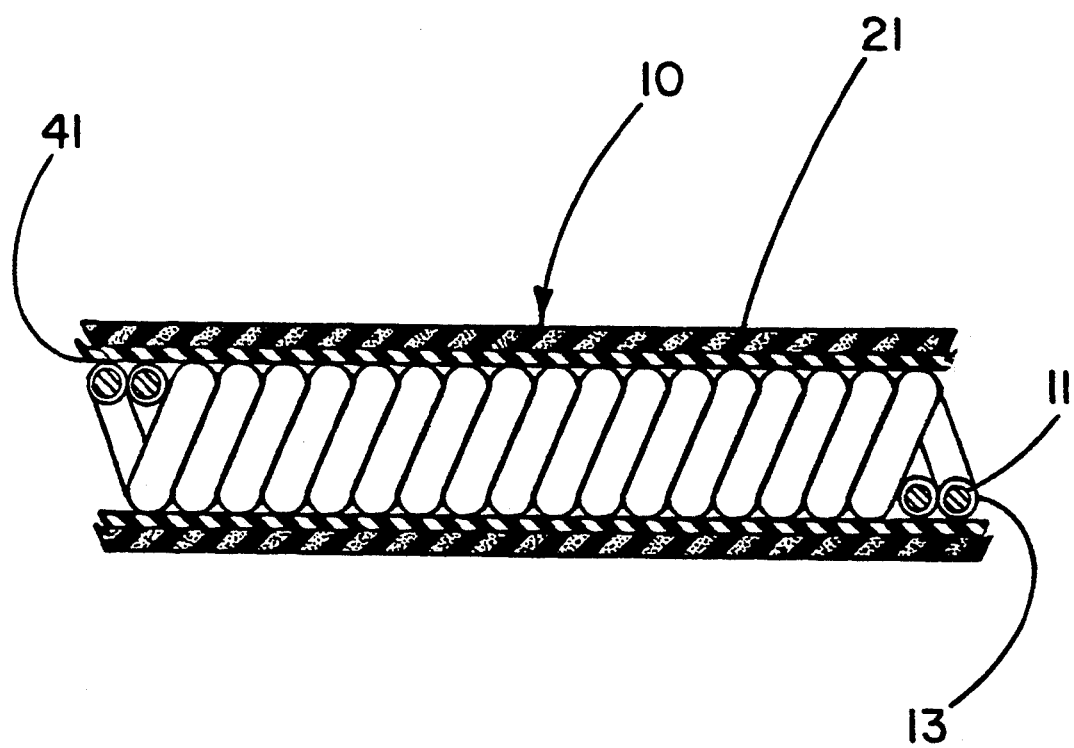
FIG. 5 shows a cross section of an alternative embodiment wherein the thermoplastic fluoropolymer insulated helically wound conductor is provided with an insulating covering of thermoplastic fluoropolymer tubing surrounded by an exterior covering of porous PTFE tubing.

FIG. 5 shows a cross section of an alternative embodiment wherein the helically wound conductor 11 having an optional insulating layer 13 is provided with an insulating covering of thermoplastic fluoropolymer tubing 41 surrounded by an exterior covering of porous PTFE tubing 21.

Figure 6:
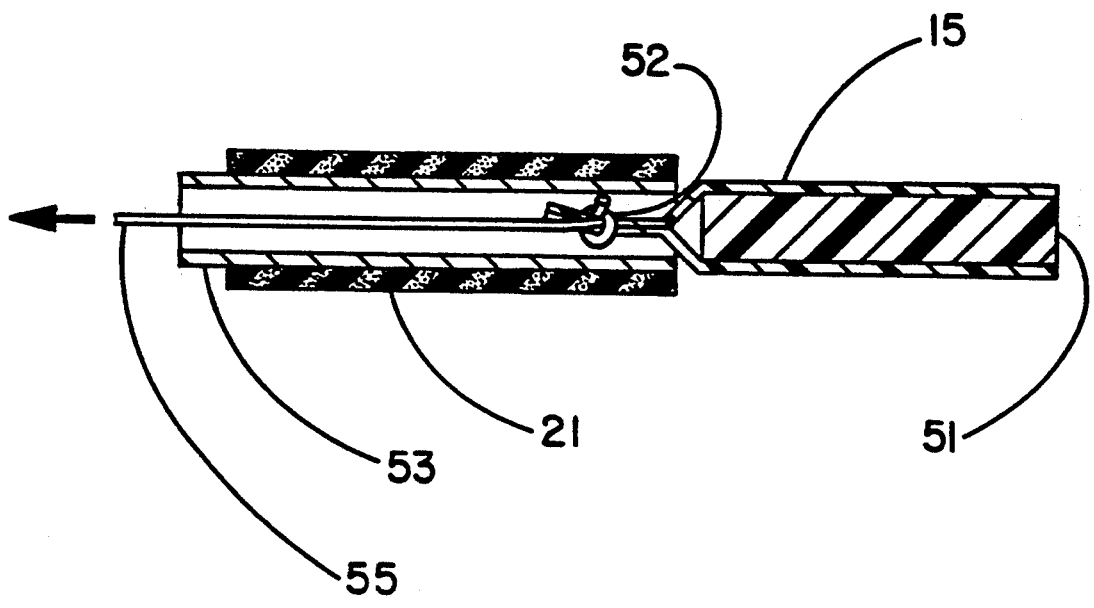
FIGS. 6 and 7 describe sequential steps in the construction of the embodiment of FIG. 2.
Figure 7:
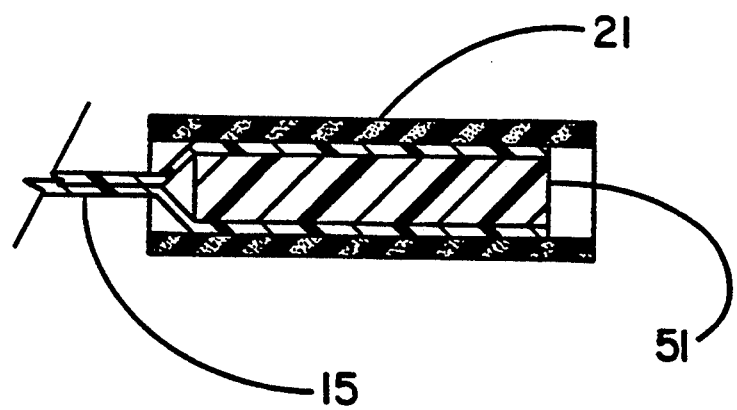

Examples of the embodiment described by FIG. 2 comprising an ETFE insulated helically wound conductor having a coaxially oriented helical wrapping of the laminated fluoropolymer tape and an exterior tubular covering of porous PTFE were made as shown by FIGS. 6 and 7. First, a construction mandrel 51 of non-porous PTFE was extruded from du Pont de Nemours (Wilmington, Del.) 6C PTFE resin. The mandrel 51 had an outside diameter of about 1.05 mm and was of round cross section. Two layers of the laminated fluoropolymer tape 15 were helically wrapped about the outer surface of mandrel 51 in opposing directions. The PTFE layer of the particular laminated tape used had been stretched longitudinally about 10:1 resulting in a reduction of the original 0.5 mm tape thickness to a thickness of about 0.025 mm. As described previously, this stretching step occurred prior to lamination of the PTFE layer to the non-porous FEP layer. The thickness of the non-porous FEP layer subsequently used for lamination to the stretched PTFE layer was about 0.012 mm. The laminated film was then expanded longitudinally about 12:1 which resulted in a porous PTFE layer and a non-porous FEP layer. The laminated tape used was of about 6.4 mm width and about 0.025 mm thickness. The laminated tape layers were wrapped at a bias angle of 55° with respect to the longitudinal axis of the mandrel.

Next, a 61 cm length of porous PTFE tubing 21 of about 18 micron fibril length, 1.0 mm inside diameter and 1.4 mm outside diameter was diametrically stretched over a 20 cm length of stainless steel tubing 53. The stainless steel tubing 53 was of about 20 cm length, 1.17 mm outside diameter and about 0.85 mm inside diameter. The porous PTFE tubing 21 was compressed longitudinally to accommodate the shorter length of the stainless steel tubing 53. Next, a 61 cm length of the tape wrapped PTFE mandrel 51 was cut from the longer length previously manufactured. A length of 0.33 mm diameter pull line 55 was tied by a knot 52 to a short length of the tape 15 covering the end of the mandrel 51 wherein the tape 15 had been unwrapped from the end of the mandrel 51 to make it available for connection to the pull line 55. The pull line 55 was used as a pull-line by inserting it through the length of the stainless steel tubing 53 and using it to pull the 61 cm length of tape-wrapped PTFE mandrel 51 against the end of the stainless steel tubing 53. When the tape-wrapped mandrel 51 was abutted against the end of the stainless steel tubing 53, the porous PTFE tubing 21 was slid off of the stainless steel tubing 53 and onto the tape-wrapped mandrel 51 so that the porous PTFE tubing 21 coaxially covered the tape-wrapped mandrel 51 as shown by FIG. 7. The length of porous PTFE tubing was then extended so that it fully covered the length of the tape-wrapped PTFE mandrel 51 and stretched even slightly beyond the ends of the mandrel. The pull line 55 was then removed from the resulting assembly, after which the assembly was placed into an oven set at 325° C. for three minutes which caused the FEP side of the laminated tape 15 to melt and adhere to the inner surface of the exterior covering of porous PTFE tubing 21. The PTFE mandrel 51 was removed by the application of enough tension to cause a reduction in the mandrel diameter adequate to allow it to release from the inner porous PTFE layer 17 of the laminated tape 15. Finally, a length of 0.15 mm diameter MP35N conductor wire, having an insulating covering of ETFE of about 0.04 mm thickness and wound into a helical form having an outside diameter of 0.84 mm, was inserted into the bore of the resulting construction as shown by FIG. 2.

A 60 cm long implantable lead wire was made according to the above description. This lead wire had a 65 cm length of helically wound unifilar conductor wire extending beyond the ends of the insulation. The entire lead wire assembly was immersed in isopropanol for about 5 minutes in order to wet out the porous PTFE. Following the wetting out procedure, the center approximately 55 cm length of this lead wire was immediately immersed in a 9 g/liter reagent grade NaCl solution for 15 minutes with the exposed ends of the helically wound conductor wire remaining above the surface of the solution. Thirty volts direct current was applied between the conductor and the solution for a period of one minute. This was done by immersing a sheet metal electrode of about 6.25 cm² in the saline solution. The leakage current resulting from this applied voltage was 0.000 microamps.

We claim:

1. An implantable lead comprising:
   a) at least one electrical conductor wire;
   b) a layer of impervious plastic insulation tubularly and coaxially surrounding the at least one electrical conductor wire; and
   c) an exterior coaxial covering comprised of porous polytetrafluoroethylene.

2. An implantable lead according to claim 1 wherein the electrical conductor wire is a helically wound electrical conductor wire.

3. An implantable lead according to claim 2 wherein the impervious plastic insulation is a laminated film comprising a layer of porous polytetrafluoroethylene and a layer of non-porous thermoplastic fluoropolymer with the layer of porous polytetrafluoroethylene facing the electrical conductor wire.

4. An implantable lead according to claim 2 wherein the impervious plastic insulation is silicone tubing and the exterior coaxial covering of porous polytetrafluoroethylene is in the form of a laminated film comprising a layer of porous polytetrafluoroethylene and a layer of non-porous thermoplastic fluoropolymer with the layer of porous polytetrafluoroethylene facing exteriorly.

5. An implantable lead according to claim 2 having a layer of porous polytetrafluoroethylene tubing coaxially covering the helically wound electrical conductor wire and lying between the helically wound electrical conductor wire and the layer of impervious plastic insulation, wherein the layer of impervious plastic insulation and the exterior coaxial covering of porous polytetrafluoroethylene comprise a laminated film having a layer of non-porous thermoplastic fluoropolymer and a layer of porous polytetrafluoroethylene with the layer of porous polytetrafluoroethylene facing exteriorly.

6. An implantable lead according to claim 2 wherein the helically wound conductor wire has a separate layer of plastic insulation covering the surface of the helically wound conductor wire.

7. An implantable lead according to claim 6 wherein the impervious plastic insulation is a laminated film comprising a layer of porous polytetrafluoroethylene and a layer of non-porous thermoplastic fluoropolymer with the layer of porous polytetrafluoroethylene facing the electrical conductor wire.

8. An implantable lead according to claim 6 wherein the impervious plastic insulation is silicone tubing and the exterior coaxial covering of porous polytetrafluoroethylene is in the form of a laminated film comprising a layer of porous polytetrafluoroethylene and a layer of non-porous thermoplastic fluoropolymer with the layer of porous polytetrafluoroethylene facing exteriorly.

9. An implantable lead according to claim 6 having a layer of porous polytetrafluoroethylene tubing coaxially covering the electrical conductor wire and lying between the electrical conductor wire and the layer of impervious plastic insulation, wherein the layer of impervious plastic insulation and the exterior coaxial covering of porous polytetrafluoroethylene comprise a laminated film having a layer of non-porous thermoplastic fluoropolymer and a layer of porous polytetrafluoroethylene with the layer of porous polytetrafluoroethylene facing exteriorly.

10. An implantable lead according to claim 1 wherein the impervious plastic insulation is silicone tubing.

11. An implantable lead according to claim 1 wherein the impervious plastic insulation is silicone tubing and the exterior coaxial covering of porous polytetrafluoroethylene is in the form of a laminated film comprising a layer of porous polytetrafluoroethylene and a layer of non-porous thermoplastic fluoropolymer with the layer of porous polytetrafluoroethylene facing exteriorly.

12. An implantable lead according to claim 11 wherein the thermoplastic fluoropolymer is selected from the group consisting of ethylenetetrafluoroethylene copolymer, fluorinated ethylene propylene and perfluoroalkoxy resin.

13. An implantable lead according to claim 1 having a layer of porous polytetrafluoroethylene tubing coaxially covering the electrical conductor wire and lying between the electrical conductor wire and the layer of impervious plastic insulation, wherein the layer of impervious plastic insulation and the exterior coaxial covering of porous polytetrafluoroethylene comprise a laminated film having a layer of non-porous thermoplastic fluoropolymer and a layer of porous polytetrafluoroethylene with the layer of porous polytetrafluoroethylene facing exteriorly.

14. An implantable lead according to claim 13 wherein the non-porous thermoplastic fluoropolymer is selected from the group consisting of ethylene-tetrafluoroethylene copolymer, fluorinated ethylene propylene and perfluoroalkoxy resin.

15. An implantable lead according to claim 1 wherein the impervious plastic insulation is a thermoplastic fluoropolymer.

16. An implantable lead according to claim 15 wherein the thermoplastic fluoropolymer is selected from the group consisting of ethylenetetrafluoroethylene copolymer, fluorinated ethylene propylene and perfluoroalkoxy resin.

17. An implantable lead according to claim 1 wherein the exterior coaxial covering of porous polytetrafluoroethylene is a porous polytetrafluoroethylene having a microstructure of nodes interconnected by fibrils, wherein the fibril length is greater than about 4 microns.

18. An implantable lead according to claims 17 wherein the fibril length is greater than about 10 microns 19. An implantable lead according to claim 17 wherein the impervious plastic insulation is a laminated film comprising a layer of porous polytetrafluoroethylene and a layer of non-porous thermoplastic fluoropolymer with the layer of porous polytetrafluoroethylene facing the electrical conductor wire.

20. An implantable lead according to claim 1 wherein the impervious plastic insulation is a laminated film comprising a layer of porous polytetrafluoroethylene and a layer of non-porous thermoplastic fluoropolymer with the layer of porous polytetrafluoroethylene facing the electrical conductor wire.

21. An implantable lead according to claim 20 wherein the non-porous thermoplastic fluoropolymer is selected from the group consisting of ethylene-tetrafluoroethylene copolymer, fluorinated ethylene propylene and perfluoroalkoxy resin.

22. A method of making an implantable lead having an impervious plastic insulating layer and an exterior covering of porous polytetrafluoroethylene tubing, comprising:
a) helically wrapping a laminated film about a mandrel, wherein the laminated film comprises a layer of porous polytetrafluoroethylene and a layer of non-porous thermoplastic fluoropolymer, with the layer of porous polytetrafluoroethylene in contact with the mandrel;
b) coaxially fitting the exterior covering of porous polytetrafluoroethylene tubing over the mandrel having the helical wrapping of laminated film;
c) heating the mandrel, laminated film and porous polytetrafluoroethylene tubing adequately to cause the thermoplastic fluoropolymer to melt, and then cooling;
d) withdrawing the mandrel to create a space and cutting off the ends of the helically wrapped film and porous polytetrafluoroethylene tubing flush with each other; and
e) inserting an electrical conductor wire into the space previously occupied by the mandrel.

* * * * *